United States Patent [19]
Schwarz

[11] Patent Number: 5,871,725
[45] Date of Patent: *Feb. 16, 1999

[54] USE OF IL-10 TO STIMULATE PERIPHERAL BLOOD MONONUCLEAR CELL CYTOLYTIC ACTIVITY

[75] Inventor: Martin A. Schwarz, Verona, N.J.

[73] Assignee: Schering Corporation, Kenilworth, N.J.

[*] Notice: The term of this patent shall not extend beyond the expiration date of Pat. No. 5,776,451.

[21] Appl. No.: 345,272

[22] Filed: Nov. 28, 1994

Related U.S. Application Data

[63] Continuation of Ser. No. 3,775, Jan. 13, 1993, abandoned.

[51] Int. Cl.$^6$ ..................................................... A61K 45/05
[52] U.S. Cl. ........................ 424/85.2; 424/85.1; 530/351; 514/21
[58] Field of Search ............................. 424/85.2; 514/21, 514/85.1; 530/351

[56] References Cited

U.S. PATENT DOCUMENTS

| | | |
|---|---|---|
| 4,690,915 | 9/1987 | Rosenberg . |
| 5,776,451 | 7/1998 | Hsu et al. ................................ 424/85.2 |

FOREIGN PATENT DOCUMENTS

| | | |
|---|---|---|
| A 0495639 | 7/1992 | European Pat. Off. . |
| 9100349 | 1/1991 | WIPO . |
| WO 92/12725 | 8/1992 | WIPO . |
| WO 92/12726 | 8/1992 | WIPO . |

OTHER PUBLICATIONS

Rosenberg et al., The New England J. Med., vol. 319 (25), pp. 1676–1680, 1988.
Gemlo et al., Cancer Res., vol. 48, pp. 5864–5867, 1988.
Spirts et al., Int. Arch. Allergy Immunol., vol. 99, pp. 8–15, 1992.
Malefyt et al., Current Opinion in Immunol., vol. 4, pp. 314–320, 1992.
Howard et al., J. Clin. Immunol., vol. 12 (4), pp. 239–247, 1992.
Kedar, et al. Cancer Immun. Immunotherapy 35: 63–68 (1992).
Spagnoli, et al. Cellular Immun. 146: 391–405 (1993).
Chen et al. J. Immunol. 147 : 528 (1991).
Edwards et al., Cancer Res. 52 : 3425 (1992).
Hsu et al., International Immunol. 4 : 563 (1992).
Kedar et al. Cancer Immunol. Immunother. 35:63 (1992).
Lotze et al. Keystone Symposia on Molecular & Cellular Biology, Jan. 26 –Feb. 10, 1993 (distributed Jan. 26, 1993).
Mule' et al. J. Immunol. 135:1 (1985).
Nagler et al. J. Immunol. 141: 2349 (1988).
Phillips et al., J. Clin. Oncol. 5: 1933 (1987).
Rosenberg, Can. Treat. Rep. 68: 233 (1984).
Spits et al. J. Immunol. 141: 29 (1988).
Swisher et al., Cell. Immunol. 128: 450 (1990).
Tepper et al., Cell 57: 503 (1989).
Thomas et al. Eur. J. Cancer 28A: 1047 (1992).
Thompson –Snipes et al., J. Exp. Med. 173: 507 (1991).

*Primary Examiner*—Chhaya D. Sayala
*Attorney, Agent, or Firm*—Cynthia L. Foulke; Norman C. Dulak; James M. Gould

[57] ABSTRACT

This invention relates to the use of IL-10, alone or in combination with IL-2 and/or α-IFN, to treat neoplastic disorders by stimulating cytolytic activity of peripheral blood mononuclear cells with IL-10 alone.

19 Claims, No Drawings

USE OF IL-10 TO STIMULATE PERIPHERAL BLOOD MONONUCLEAR CELL CYTOLYTIC ACTIVITY

This is a continuation of application Ser. No. 08/003,775 filed Jan. 13, 1993 now abandoned.

FIELD OF THE INVENTION

This invention relates to the use of Interleukin-10 (IL-10), formally cytokine synthesis inhibitory factor (CSIF), for adoptive immunotherapy in the treatment of neoplastic disorders (cancer) by stimulation of cytolytic activity of peripheral blood mononuclear cells (PBMC).

BACKGROUND OF THE INVENTION

Immunologic approaches to cancer therapy are based on the notion that cancer cells have somehow evaded the body's defenses against aberrant or foreign cells and molecules, and that these defenses might be therapeutically stimulated to kill or inhibit the growth of the cancer cells, e.g., as discussed by Klein (*Immunology*, Wiley-Interscience, New York, 1982, pp. 623–648). The recent observation that immune effectors can directly or indirectly inhibit tumor growth has led to renewed interest in this approach to cancer therapy [Heberman, Concepts Immunopath. 1:96 (1985) (natural killer cells resist tumor growth); Rosenberg et al., Ann. Rev. Immunol. 4:681 (1988) (use of IL-2-activated killer cells to treat cancer); Ralf et al., J. Exp. Med. 167:712 (1988) (tumoricidal activity of macrophages stimulated by lymphokines); Tepper et al., Cell 57:503 (1989) (IL-4 has tumoricidal activity); M. Cohen, "Lymphokines and Tumor Immunity", pp. 237–253, in S. Cohen, ed., *Lymphokines and the Immune Response* (CRC Press, Boca Raton, 1990)].

Immune responsiveness to neoplasms is regulated by a variety of cell types and involves the actions of T-cell and monocyte-derived cytokines. One immunologic approach that has shown clinical promise has been so-called "adoptive immunotherapy" using IL-2-activated killer cells [Rosenberg, supra; Rosenberg, Sci. Am., pp. 62–69 (May 1990)]. Although IL-2 alone or in combination with more traditional chemotherapeutic agents appears to be effective in treating certain malignancies (e.g., renal cell carcinoma), unfortunate toxic side effects such as vascular bed leakage and edema associated with administration of effective dosages of IL-2 have led some to suggest that the risks may outweigh the benefits [Cotran et al., J. Immunol. 139:1882 (1987); Edwards et al., Cancer Res. 52:3425 (1992)].

Human vascular endothelial cells appear to be particularly sensitive to IL-2 toxicity, as evidenced by increased vascular permeability (i.e. vascular leak syndrome) and edema. One of the factors contributing to this pathology may be augmented adhesion of IL-2-activated T cells and neutrophils to endothelial monolayers, as has previously been noted in vitro [Edwards et al., supra; Damle et al., 138:1779 (1987)].

An alternative therapeutic approach to the immunologic treatment of neoplastic disease is the adoptive transfer of immune cells. Adoptive immunotherapy is defined as the transfer to a tumor-bearing host of active immunologic reagents, such as cells with anti-tumor activity that can mediate, either directly or indirectly, anti-tumor effects. Adoptive immunotherapy represents an attractive approach to the therapy of neoplastic disease. It should be noted that because active immunologic reagents are being transferred to the host, complete host immunocompetence is not required. Thus, the immunosuppression generally associated with the tumor-bearing state does not represent a major problem to this therapeutic alternative. Since host immunocompetence is not required, and in fact may be beneficial to the effects of the adoptive transfer of immune cells, adoptive immunotherapy can easily be combined with other therapies such as chemotherapy or radiation therapy. Also, in contrast to other therapies, immunosuppression is unlikely to result from this treatment.

Patients undergoing chemotherapy or radiation therapy tend to be immunocompromised and will generally have a depleted supply of effector peripheral blood mononuclear cells (PBMCs) available for activation. A therapy that shows efficacy at low effector cell:target cell ratios would thus be particularly advantageous for such patients.

Immune responsiveness to neoplasms is regulated by a variety of cell types and involves the actions of T-cell and monocyte-derived cytokines. Adoptive immunotherapy using recombinant human cytokines has involved administration of peripheral blood mononuclear cells (PBMCs) stimulated extra-corporeally [Phillips et al., J. Clin. Oncol. 5:1933:(1987); Perussia, Curr. Opin. Immunol. 3:49:(1991)] followed by administration of IL-2 [Rosenberg et al., J. Immunol. 138:1779 (1985)]. The extra-corporeal treatment of the PBMCs produces activated lymphokine-activated killer (LAK) cells and activated natural killer (NK) cells having cytolytic activity for various tumor cells.

Recombinant human IL-5 [Nagasawa et al., Cell. Immunol. 133:317 (1991)], IL-7 [Stotter and Lotze, Arch. Surgery 126:1525 (1991)] and IL-12 [Gately et al., J. Immunol. 147:874 (1991)] have been reported to stimulate cytolytic activity in human PBMCs. Interleukin-10 (IL-10), originally described in mice as a cytokine synthesis inhibitory factor secreted by specific helper T-cell subsets, appears to modulate the differentiation of murine cytotoxic T-cells [Chen and Zlotnik, J. Immunol 147:528 (1991)]. It has also been found that human PBMCs incubated with supernatants recovered from COS cells transfected with the human IL-10 cDNA lysed tumor cell targets in vitro. The T cells responding to IL-10 with increased cytolytic potential were identified to be of a CD56+ phenotype, indicative of NK cells.

In some circumstances, IL-4 can adversely affect the generation of LAK activity by IL-2 [Nagler et al., J. Immunol. 141:2349 (1988)]. For example, if human PBMCs are cultured in the presence of both IL-2 and IL-4, the lysis of LAK-sensitive targets is greatly reduced [Spits et al., J: Immunol. 141:29 (1988)]. If the PBMCs are pre-cultured in medium supplemented with IL-2 for 3 days before adding IL-4, however, augmented cytolytic activity results [Spits et al., supra]. Moreover, the blockade of IL-2-driven cytotoxicity by IL-4 can be abated when alpha-interferon ($\alpha$-IFN) or tumor necrosis factor-alpha (TNF-$\alpha$) is included in the initial incubation mixture [Swisher et al., Cell. Immunol. 128:450 (1990)].

Kedar et al., [Cancer Immunol. Immunother. 35:63 (1992)] have recently indicated that sequential administration of IL-2 and $\alpha$-IFN is an effective immunotherapeutic regimen for treatment of MCA-105 sarcomas and M109 carcinomas in murine tumor models. The primary finding from this study was that sequential administration of cytokines appeared to have greater efficacy than concomitant administration of both cytokines.

The feasibility and efficacy of adoptive immunotherapy as a treatment modality for various diseases, particularly for the treatment of neoplastic disease (cancer) in humans, have been described in U.S. Pat. No. 4,690,915 to Rosenberg. As already noted above, however, there is a need for methods for carrying out such treatments that are not as toxic as those employing IL-2 alone. There is also a need for a therapy that is effective at low effector cell:target cell ratios.

SUMMARY OF THE INVENTION

The present invention fills these needs by providing methods for the use of IL-10 alone or in combination with IL-2 and/or α-IFN to augment cytolytic activity of PBMCs, especially LAK and NK cells.

More particularly, this invention provides a method for treating cancer comprising administering to a patient afflicted with cancer an effective amount of IL-10 and IL-10-activated PBMCs, to cause regression of such cancer.

In one embodiment, the IL-10 is administered in combination with an amount of IL-2 sufficient to augment LAK cell activation but not to cause toxic side effects attributable to the use of IL-2 alone.

In another embodiment the IL-10 is administered in combination with an amount of α-IFN sufficient to augment LAK cell activation.

In still another embodiment the IL-10 is administered in combination with (a) an amount of IL-2 sufficient to augment LAK cell activation but not to cause toxic side effects attributable to the use of IL-2 alone and with (b) an amount of α-IFN sufficient to augment LAK cell activation.

This invention further provides a method for antagonizing blockade of IL-2-induced cytotoxicity by endogenous IL-4 comprising administering to a patient in need of such treatment an effective amount of IL-10.

This invention still further provides pharmaceutical compositions comprising IL-10 in combination with IL-2 and/or α-IFN, and a pharmaceutically acceptable carrier.

Preferably, human IL-10, IL-2 and α-IFN are used in the foregoing methods and compositions, most preferably, recombinant human IL-10, IL-2 and α-IFN.

DESCRIPTION OF THE INVENTION

All references cited herein are hereby incorporated in their entirety by reference.

The present invention is an improvement over methods of the prior art which employ IL-2 to induce cytolytic activity in NK and LAK cells. The present invention greatly reduces the toxic side effects that typically result from the use of IL-2 in such methods by eliminating the IL-2 completely, or greatly reducing the amount of IL-2 that must be used.

Unless defined otherwise, the various terms used herein have the same meanings as are well understood in the art to which this invention is directed.

As used herein the term "adoptive immunotherapy" means therapy involving the transfer of activated functional immune cells to a patient. Preferably, these cells will comprise LAK and NK cells originating from the actual patient undergoing treatment.

The term "regression" is defined herein to mean a measurable decrease in the size of one or more tumors, as commonly measured in the art.

As used herein, "interleukin-10" or "IL-10" is defined as a protein which (a) has an amino acid sequence of mature (e.g., lacking a secretory leader sequence) IL-10 as disclosed in U.S. patent application Ser. No. 07/917,806, filed Jul. 20, 1992, which corresponds to International Application No. WO 91/00349, and (b) has biological activity that is common to native IL-10. For the purposes of this invention both glycosylated (e.g. produced in eukaryotic cells such as CHO cells) and unglycosylated (e.g., chemically synthesized or produced in *E. coli*) IL-10 are equivalent and can be used interchangeably. Also included are muteins and other analogs, including BCRF1 (Epstein Barr Virus viral IL-10) protein, which possess the biological activity of IL-10.

IL-10 suitable for use in the invention can be obtained from a number of sources. For example, it can be isolated from culture medium of activated cells secreting the protein. Additionally, the IL-10, or active fragments thereof can be chemically synthesized using standard techniques known in the art. See Merrifield, Science 233:341 (1986) and Atherton et al., *Solid Phase Peptide Synthesis: A Practical Approach*, 1989, I.R.L. Press, Oxford.

Preferably, the protein or polypeptide is obtained by recombinant techniques using isolated nucleic acid encoding the IL-10 polypeptide. General methods of molecular biology are described, e.g., Sambrook et al., *Molecular Cloning, A Laboratory Manual*, Cold Spring Harbor, N.Y., 2d ed., 1989, and by Ausubel et al., (eds.) *Current Protocols in Molecular Biology*, Green/Woley, New York (1987 and periodic supplements). The appropriate sequences can be obtained using standard techniques from either genomic or cDNA libraries. Polymerase chain reaction (PCR) techniques can be used. See, e.g., *PCR Protocols: A Guide to Methods and Applications*, 1990, Innis et al., (Ed.), Academic Press, New York, N.Y.

Libraries are constructed from nucleic acid extracted from appropriate cells, see, for example, International Application Publication No. WO 91/00349, which discloses recombinant methods for making IL-10. Useful gene sequences can be found, e.g., in various sequence databases, e.g., GenBank and BMPL or nucleic acid and PIR and Swiss-Prot for protein, c/o Intelligenetics, Mountain View, Calif. or the Genetics Computer Group, University of Wisconsin Biotechnology Center, Madison, Wis., which are incorporated herein by reference.

Clones comprising sequences that encode human IL-10 have been deposited with the American Type Culture Collection (ATCC), Rockville, Md., under Accession Nos. 68191 and 68192. Identification of other clones harboring the sequences encoding IL-10 is performed by either nucleic acid hybridization or immunological detection of the encoded protein, if an expression vector is used. Oligonucleotide probes based on the deposited sequences disclosed in International Application Publication No. WO 91/00349 are particularly useful. Oligonucleotide probes sequences can also be prepared from conserved regions of related genes in other species. Alternatively, degenerate probes based on the amino acid sequences of IL-10 can be used.

Standard methods can be used to produce transformed prokaryotic, mammalian, yeast or insect cell lines which express large quantities of the polypeptide. Exemplary *E. coli* strains suitable for both expression and cloning include W3110 (ATCC Bi, 27325), X1776 (ATCC No. 31244). X2282, RR1 (ATCC Mp/31343). Exemplary mammalian cell lines include COS-7 cells, mouse L cells and CHP cells. See Sambrook (1989) and Ausubel et al., 1987 supplements).

Various expression vectors can be used to express DNA encoding IL-10. Conventional vectors used for expression of recombinant proteins in prokaryotic or eukaryotic cells may be used. Preferred vectors include the pcD vectors described by Okayama et al., Mol. Cell. Biol. 3:280 (1983); and Takebe et al., Mol. Cell. Biol. 8:466 (1988). Other SV40-based mammalian expression vectors include those disclosed in Kaufman et al., Mol. Cell. Biol. 2:1304 (1982) and U.S. Pat. No. 4,675,285. These SV40-based vectors are particularly useful in COS-7 monkey cells (ATCC No. CRL 1651), as well as in other mammalian cells such as mouse L cells. See also, Pouwels et al., (1989 and supplements) *Cloning Vectors: A Laboratory Manual*, Elsevier, N.Y.

The IL-10 can be produced in soluble form such as a secreted product of transformed or transfected yeast or mammalian cells. The peptides can then be purified by standard procedures that are known in the art. For example, purification steps could include ammonium sulfate precipitation, ion exchange chromatography, gel filtration, electrophoresis, affinity chromatography, and the like. See *Methods in Enzymology Purification Principles and Practices* (Springer-Verlag, N.Y., 1982).

Alternatively, IL-10 may be produced in insoluble form such as aggregates or inclusion bodies. The IL-10 in such a form is purified by standard procedures that are well known in the art. Examples of purification steps include separating the inclusion bodies from disrupted host cells by centrifugation, and then solubilizing the inclusion bodies with chaotropic agent and reducing agent so that the peptide assumes a biologically active conformation. For specifics of these procedures, see, e.g. Winkler et al., Biochemistry, 25:4041 (1986), Winkler et al., Bio/Technology 3:9923 (1985); Koths et al., and U.S. Pat. No. 4,569,790.

The nucleotide sequences used to transfect the host cells can be modified according to standard techniques to make IL-10 or fragments thereof with a variety of desired properties. Such modified IL-10 can vary from the naturally-occurring sequences at the primary structure level, e.g., by amino acid, insertions, substitutions, deletions and fusions. These modifications can be used in a number of combinations to produce the final modified protein chain.

The amino acid sequence variants can be prepared with various objectives in mind, including increasing serum half-life, facilitating purification or preparation, improving therapeutic efficacy, and lessening the severity or occurrence of side effects during therapeutic use. The amino acid sequence variants are usually predetermined variants not found in nature, although others may be post-translational variants, e.g., glycosylated variants or proteins which are conjugated to polyethylene glycol (PEG), etc. Such variants can be used in this invention as long as they retain the biological activity of IL-10.

Modifications of the sequences encoding the polypeptides may be readily accomplished by a variety of techniques, such as site-directed mutagenesis [Gillman et al., Gene 8:81 (1987)]. Most modifications are evaluated by routine screening in a suitable assay for the desired characteristics. For instance, International Application Publication No. WO 91/00349 describes a number of in vitro assays suitable for measuring IL-10 activity.

Preferably, human IL-10 is used for the treatment of humans, although viral IL-10 or IL-10 from some other mammalian species could possibly be used. Most preferably, the IL-10 used is recombinant human IL-10. The preparation of human and mouse IL-10 has been described in International Application WO 91/00349. The cloning and expression of viral IL-10 (BCRF1 protein) from Epstein Barr virus has been disclosed by Moore et al., Science 248:1230 (1990). Recombinant human IL-10 is also an article of commerce, available for purchase e.g., from PreproTech, Inc., Rocky Hill, N.J.

Individuals suitable for treatment by the methods of this invention include any individual with a neoplastic disorder that would benefit from stimulation of PBMC cytolytic activity, especially LAK and NK cell activation. Exemplary cancer patients are described, e.g., in the patent and Scientific American paper of Rosenberg, supra. Also suitable for treatment by the methods of this invention are individuals predisposed to elevations of endogenous IL-4 levels, such that the IL-4 blocks the IL-2 activation of cytolytic activity. In such individuals, the preferred treatment would involve pre-treatment with IL-10 prior to the administration of IL-2.

The standard methods and techniques described for making IL-10 for use in this invention can also be employed to make IL-2 and α-IFN. IL-2 and α-IFN for use in this invention are also available from commercial sources (e.g., IL-2 is available from Cetus, Corporation, Emeryville, Calif. and α-IFN is available from Schering Corp., Kenilworth, N.J.).

Extra-corporeal activation of PBMCs (preferably obtained by standard methods from a patient that is to be treated) and administration of such cells are carried out essentially as described in the references of Rosenberg mentioned above, except that IL-10 together with reduced levels of IL-2 and/or α-IFN are used as described herein. The number of activated PBMCs administered is in the range of about $10^6$ to about $10^{12}$ cells. Preferably, although not necessarily, administration of such activated cells is accompanied and/or followed by administration of IL-10 as described herein.

Administration of cytolytic cells activated by IL-10, alone or in combination with the other cytokines used herein, is preferably by intravenous infusion. This can be carried out, e.g., through a central venous catheter, into a large peripheral vein, or into the hepatic artery via a percutaneous catheter.

IL-10 is generally administered as a pharmaceutical composition comprising a pharmaceutical carrier and effective amount of IL-10 alone or in combination with IL-2 and/or α-IFN. A pharmaceutical carrier can be any compatible non-toxic substance suitable for delivery of the invention to a patient. Compositions useful for parenteral administration of such drugs are well-known, e.g., see *Remington's Pharmaceutical Science*, 15th Ed. (Mack Publishing Company, Easton, Pa., 1980). Alternatively, compositions of the invention may be introduced into a patient's body by implantable or injectable drug delivery system, e.g., Urquhart et al., Ann. Rev. Pharmacol. Toxicol. 24:199 (1984); Lewis (Ed.), *Controlled Release of Pesticides and Pharmaceuticals* (Plenum Press, NY,1981); U.S. Pat. No. 3,270,960; and the like.

Cytokine administration can be carried out by any of the well known routes of administration, including by intravenous, intraperitoneal and subcutaneous administration. Intravenous administration is preferred.

When administered parenterally, the compositions are formulated in a unit dosage injectable form (solution, suspension, emulsion) in association with a pharmaceutical carrier. Examples of such carriers are normal saline, Ringer's solution, dextrose solution, and Hank's solution. Non-aqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. The IL-10 is preferably formulated in purified form substantially free of aggregates and other proteins at a concentration in the range of about 5 to 20 µg/ml.

The compositions of this invention can also be delivered by standard gene therapy techniques, including e.g., direct DNA injection into tissues, the use of recombinant viral vectors and implantation of transfected cells. See, e.g., Rosenberg, J. Clin. Oncol. 10:180 (1992).

Co-administration of one or more of the therapeutic agents described herein can be concomitant (together with the administration of the IL-10) or sequential. Preferably, the IL-10 is administered prior to the administration of the IL-2. Administration of α-IFN can be concomitant with the IL-10 and/or the IL-2 or sequential. All of the administered agents should be present in the patient at sufficient levels to be therapeutically effective in producing tumor regression.

As used herein the term "effective amount" means the amount of IL-10 sufficient to reduce or prevent side effects in adoptive immunotherapy and to at the same time promote LAK and NK cell cytolytic activity. The effective amount of cytokine(s) needed for a particular patient may vary depending on such factors as the state and type of the neoplastic disease being treated, the overall health of the patient, methods of administration, the severity of the side effects, the amount and kinds of other drugs being used concurrently, and the like.

An amount of a cytokine "sufficient to augment LAK cell activation" is defined herein to mean an amount of a cytokine required to produce at least about a 25% increase in the level of cytolytic activity induced by IL-10 alone, in a cytolytic assay based on Daudi cells. Preferably the increase will be at least about 50%, and most preferably, at least about 100%.

Preferably, the IL-10 is administered in the maximally tolerable dose, from about 10 U/kg body weight per day to about $10^8$ U/kg body weight per day. Likewise, IL-2 and α-IFN are also to be administered in the maximally tolerable dose (e.g., for the IL-2 dose: $10^5$ U/kg body weight given intravenously every 8 hours in 50 ml of 0.9% saline with 5% albumin as a carrier; for the α-IFN dose: $10^6$ U/kg body weight given intravenously every 8 hours in 0.9% saline with 5% albumin as a carrier). As previously stated, dosing is to be adjusted by attending physician to fall within those limits determined to be tolerable for each patient individually.

The methods of this invention can also be used in conjunction with traditional approaches to the treatment of cancer, such as radiation therapy and chemotherapy, using traditional chemotherapeutic agents such as the Vinca alkaloids, platinum compounds and 5-fluorouracil.

EXAMPLE

The following non-limiting Example will serve to illustrate the present invention.

Effect of IL-10 on Cytolytic Activity in Human Peripheral Blood Mononuclear Cells The effect of IL-10 on in vitro generation of cytolytic activity in human peripheral blood mononuclear cells was studied. Results can be summarized as follows:

1. IL-10 stimulates lymphokine activated killing (LAK) and natural killer (NK) activities in human peripheral blood mononuclear cells. IL-10 driven cytolytic activity can be neutralized by rat monoclonal antibodies against IL-10.

2. IL-10 derived from CHO and *E. coli* expression systems display similar concentration response patterns in stimulation of LAK and NK activities and are thus biologically equivalent.

3. PBMCs treated with IL-10 and low concentrations of IL-2 display LAK activities greater than observed with either cytokine alone.

4. PBMCs pre-treated with IL-10 for 2 days demonstrate increased cytolytic activity upon subsequent addition of IL-2.

5. IL-10 antagonizes the ability of IL-4 to inhibit IL-2-induced LAK activity.

6. IL-10 plus IL-2 produces enhanced LAK cytolytic activity at low effector cell:target cell ratios.

In addition to the effects observed on PBMCs, it was found that endothelial cells cultured in the presence of IL-10 demonstrate an unimpaired response to exogenous factors (i.e., to γ-IFN and to TNF-α), whereas endothelial cells incubated in the presence of IL-2 were unresponsive due to IL-2 toxicity.

Materials and Methods

Recombinant human cytokines and anti-IL-10 antibodies

Recombinant human IL-10 (both *E. coli*- and CHO-derived) was produced by standard methods. Specific activities obtained following purification by standard methods were $4.1 \times 10^7$ (*E. coli*) and $2.1 \times 10^7$ units/mg (CHO), as determined by the MC-9 cell proliferation assay [Thompson-Snipes et al., *J. Exp. Med.* 173:507 (1991)]. Approximately 4 ng of essentially homogeneous IL-10 had about 100 units of biological activity as thus defined.

A rat anti-human IL-10 monoclonal antibody designated 19F1 was obtained from Dr. John Abrams of the DNAX Institute of Molecular Biology, Palo Alto, Calif.

Isolation of human peripheral blood mononuclear cells (PBMCs)

Peripheral blood was obtained by venipuncture from healthy adult donors using heparin or EDTA as an anticoagulant. PBMCs were separated by a two-step protocol consisting of dextran sedimentation followed by centrifugation on FICOLL PAQUE® at 1250 rpm for 30 minutes. The interface bands comprised primarily of lymphocytes and monocytes were collected and washed at least twice with RPMI containing 10% fetal calf serum (complete medium) (JRH Biosciences).

Cytotoxicity Assays

Daudi (LAK-sensitive) and K562 (NK-sensitive) target cells were obtained from American Type Tissue Collection under accession Nos. CCL 213 and CCL 243, respectively. Daudi and K562 were labelled with $^{51}$Cr as described by Spits et al., [J. Immunol. 141:29 (1998)]. After the culture period, PBMCs were harvested, washed twice, and used as effector cells in a $^{51}$Cr-release assay (Spits et al., supra). $5 \times 10^3$ $^{51}$Cr-labelled target cells were mixed with varying numbers of effector cells (E/T=20:1; 5:1 and 2:1) in 100 μl in V-shaped bottom 96-well plates. The plates were centrifuged for 5 minutes at 1000 rpm before incubation for 4 hours at 37° C. in a humidified 5% $CO_2$ atmosphere. After 4 hours the plates were centrifuged for 5 minutes at 500×g. Supernatants were collected using a SKATRON® harvester (Skatron Instruments) and counted in a gamma counter (LKB-Pharmacia). Total lysis was determined by incubating $^{51}$Cr-labelled targets with 1% SDS. Data were represented as the mean of triplicate determinations.

Percent lysis was calculated as follows:

$$\% \text{ lysis} = \frac{cpm \text{ released experimental} - cpm \text{ spontaneous}}{cpm \text{ total lysis} - cpm \text{ spontaneous}} \times 100$$

Incubation of Human PBMCs with Cytokines a. Incubation with IL-10 alone

PBMCs isolated as described above were maintained at a concentration of $1 \times 10^6$ cells/ml in RPMI-1640 containing 10% fetal calf serum supplemented with IL-10 or human IL-10 (CHO) at 37° C. for 3 days unless otherwise specified. Cytolytic activity was determined as described above.

b. Simultaneous incubation with IL-10 and IL-2

PBMCs were incubated with 4 ng/ml IL-10 with or without human IL-2 (Genzyme) (2 or 20 U/ml) at 37° C. for 3 days.

c. Sequential incubation with IL-10 and IL-2

PBMCs were incubated with 4 ng/ml IL-10 in complete medium for 2 days. Human IL-2 was added to a final concentration of 2 or 20 U/ml. After overnight incubation, LAK and NK cytolytic activities were determined.

Effect of Anti-IL-10 Monoclonal Antibodies on IL-10 Activation of LAK and NK Cells PBMCs were incubated with 40 ng/ml IL-10 for 3 days in the presence of 2 μg/ml of an anti-IL-10 monoclonal antibody (19F1) or an isotypic control (rat IgG2a).

Effect of IL-10 on Lymphokine-Activated Killer Cell and Natural Killer Cell Cytolytic Activity in Human Peripheral Blood Mononuclear Cells Cytolytic activity of LAK and NK cells can be operationally distinguished based on the tumor cell target used. Daudi cells, derived from a human Burkitt's lymphoma, are the traditional targets for activated LAK cell cytolytic activity. Cells from the K562 cell line, a human erythroleukemic cell line, are employed as specific targets for the cytolytic activity of activated NK cells. In these experiments human PBMCs were treated with various concentrations of IL-10 for 3 days. Cytolytic activity was determined in a standard $^{51}$Cr release assay as described above.

Results based on LAK activity are shown in Table 1, in which standard errors are shown below the mean values.

TABLE 1

Stimulation of Lymphokine-Activated PBMCs by IL-10 (expressed as % Lysis[a])

| Donor | Concentration of IL-10 (ng/ml)[b] | | | | | |
|---|---|---|---|---|---|---|
| | 0 | 0.04 | 0.4 | 4 | 40 | 100 |
| 1 | 0 | 4.25 | 18.3 | 44 | 26.2 | 67.5 |
| 2 | 0 | 5.5 | 7.2 | 10 | 31.5 | 27.6 |
| 3 | 18 | 17.7 | 29.2 | 39.1 | 29.7 | 55.1 |
| 4 | 0 | 8.8 | 10.2 | 22.2 | 35.8 | 35.9 |
| 5 | 4.6 | 8.1 | 15.6 | 20.6 | 20.1 | 12.1 |
| 6 | 14.6 | 19.7 | 40.7 | 54.4 | 42.9 | 43.4 |
| Mean: | 6.2 ± 3.3 | 10.6 ± 2.6 | 20.2[c] ± 5.1 | 31.7[c] ± 6.8 | 31.0[c] ± 3.2 | 40.2[c] ± 8.0 |

[a]Percent lysis of $^{51}$Cr Daudi targets in standard chromium release assay at an effector to target ratio of 20:1. Data are represented as the mean of triplicate determinations.
[b]Human PBMCs prepared from normal donors were treated with IL-10 for 3 days before determination of cytolytic activity.
[c]Significant difference between IL-10 treated and medium control at p ≤ 0.05 as determined by Student's t-test.

The data of Table 1 show the effect of IL-10 on LAK activity in PBMCs obtained from six human donors. Although variability among the donors was evident, IL-10 induced a concentration-dependent increase in cytolytic capacity in all 6 donors. Statistically significant activity (p≤0.05) was observed at concentrations of IL-10 of 0.4 ng/ml or greater. It was also observed that donor PBMCs displaying a basal level of cytolytic activity (i.e., in the absence of cytokine) of 5% or less were most responsive to IL-10 at all effector cell:target cell ratios tested (data not shown).

Similar results were obtained against other tumor target cells, including a human renal cell carcinoma line, two different human melanoma lines and a human colon carcinoma line. The renal carcinoma and melanoma cell lines have also been used by Rosenberg, and patients bearing such tumors have been treated in vivo by Rosenberg using adoptive immunotherapy with IL-2. In all cases, percent lysis of target cells was IL-10 concentration dependent.

Basal NK cytolytic activity (i.e., lysis of K562 targets in the absence of cytokines) tends to be higher than basal LAK activity. NK activity can be further increased by cytokines such as IL-2 [Perussia, supra; Phillips and Lanier, J. Exp. Med 164:814 (1986)].

The effect of IL-10 on NK activity was evaluated in PBMCs from the same 6 donors mentioned above, in experiments run in parallel with the LAK assays. The results are shown in Table 2, in which standard errors are shown below the mean values.

TABLE 2

Stimulation of NK Activity (expressed as % lysis[a]) in PBMCs by IL-10

| Donor | Concentration of IL-10 (ng/ml)[b] | | | | | |
|---|---|---|---|---|---|---|
| | 0 | 0.04 | 0.4 | 4 | 40 | 100 |
| 1 | 22.2 | 30.6 | 25.2 | 57.2 | 51.5 | 49.7 |
| 2 | 20.4 | 24.7 | 31.3 | 56.7 | 65.6 | 71.5 |
| 3 | 61.4 | 55.6 | 37.9 | 81.1 | 80.0 | 81.5 |
| 4 | 13.8 | 25.2 | 23.2 | 37.5 | 52.2 | 54.2 |
| 5 | 13.0 | 19.9 | 20.2 | 25.1 | 23.5 | 20.3 |
| 6 | 15.9 | 25.3 | 45.4 | 66.6 | 43.7 | 56.1 |
| Mean: | 24.4 ± 7.5 | 30.2 ± 5.2 | 30.5 ± 3.9 | 54.0[c] ± 8.2 | 52.75[c] ± 7.8 | 55.5[c] ± 8.5 |

[a]Percent lysis of $^{51}$Cr Daudi targets in standard chromium release assay at an effector to target ratio of 20:1. Data are represented as the mean of triplicate determinations.
[b]Human PBMCs prepared from normal donors were treated with IL-10 for 3 days before determination of cytolytic activity.
[c]Significant difference between IL-10 treated and medium control at p ≤ 0.05 as determined by Student's t-test.

As is evident from Table 2, IL-10 induced a significant dose-dependent enhancement of NK-cell mediated cytotoxicity in PBCMs from the donors. There was a statistically-significant increase in lytic activity at concentrations of IL-10 of 4 ng/ml or greater. As in the case of LAK activity, the effect of IL-10 on NK activity varied from donor to donor.

Comparison of Effects of IL-2 versus IL-10 on Endothelial Cells

Experiments were conducted to evaluate endothelial cell monolayer viability following exposure to IL-10. Endothelial cells cultured in the presence of IL-10 demonstrated an unimpaired response to exogenous cytokines (γ-IFN and TNF-α), whereas parallel cultures exposed to unit-equivalent doses of IL-2 for the same incubation period lost the capacity to respond due to IL-2 toxicity.

Effect of Anti-IL-10 Monoclonal Antibodies on IL-10 Activation of LAK and NK Cells As shown in Tables 3 and 4, where mean values are shown with standard errors, the stimulation of LAK and NK cytolytic activities, respectively, by 40 ng/ml IL-10 were reduced 3-fold (p≤0.05) in the presence of 2 μg/ml anti-IL-10 monoclonal antibody 19F1. Results produced using 2 μg/ml rat IgG2a isotypic control antibodies instead produced levels of cytolytic activity that were statistically indistinguishable from those obtained using 40 ng/ml IL-10 alone.

TABLE 3

Inhibition of IL-10-Induced Lymphokine-Activated
Killer Cell Cytolytic Activity (expressed as % lysis[a]) by
Anti-IL-10 Monoclonal Antibodies

| | | Incubation Conditions[b] | | |
|---|---|---|---|---|
| Donor | medium | 40 ng/ml IL-10 | IL-10 + 19F1 | IL-10 + IgG2a |
| 1 | 5.6 | 23.5 | 15.7 | 28.2 |
| 2 | 4.7 | 21.3 | 11.0 | 17.5 |
| 3 | 5.4 | 42.5 | 0.0 | 35.8 |
| 4 | 2.1 | 42.0 | 12.8 | 26.5 |
| 5 | 4.7 | 19.1 | 0.0 | 11.65 |
| Mean | 4.5 ± 0.6 | 29.6 ± 5.3 | 7.9[c] ± 3.3 | 23.9 ± 4.3 |

[a]Percent lysis of [$^{51}$Cr] Daudi targets in standard chromium release assay at an effector:target ratio of 20:1. Data are represented as the mean of triplicate determinations.
[b]Human peripheral blood mononuclear cells isolated from normal donors were treated with 40 ng/ml IL-10 for 3 days in the presence of 2 mg/ml 19F1(anti human IL-10) or rat IgG2a (isotypic control) before determination of cytolytic activity.
[c]Significant difference between IL-10 treatment alone and IL-10 treatment in the presence of anti IL-10 antibodies at $p \leq 0.05$ as determined by Student's t-test.

TABLE 4

Neutralization of IL-10-Induced Natural Killer Cell
Activity (expressed as % lysis[a]) by Anti-IL-10
Monoclonal Antibodies

| | | Incubation conditions[b] | | |
|---|---|---|---|---|
| Donor | medium | 40 ng/ml IL-10 | IL-10 + 19F1 | IL-10 + IgG2a |
| 1 | 21.1 | 38.3 | 20.6 | 27.2 |
| 2 | 28.0 | 71.0 | 22.2 | 53.2 |
| 3 | 22.2 | 51.5 | 0.0 | 70.5 |
| 4 | 18.0 | 25.4 | 12.3 | 20.8 |
| 5 | 23.2 | 53.2 | 54.5 | 84.9 |
| Mean | 22.5 ± 1.6 | 47.9 ± 7.6 | 19.1[c] ± 6.6 | 51.3 ± 12.7 |

[a]Percent lysis of [$^{51}$Cr] Daudi targets in standard chromium release assay at an effector:target ratio of 20:1. Data are represented as the mean of triplicate determinations.
[b]Human peripheral blood mononuclear cells isolated from normal donors were treated with 40 ng/ml IL-10 for 3 days in the presence of 2 mg/ml 19F1(anti human IL-10) or rat IgG2a (isotypic control) before determination of cytolytic activity.
[c]Significant difference between IL-10 treatment alone and IL-10 treatment in the presence of anti IL-10 antibodies at $p \leq 0.05$ as determined by Student's t-test.

Cytolytic Activity Induced by Combinations of IL-10 and Other Cytokines a. Simultaneous Incubation with IL-10 and IL-2

Human PBMCs were incubated with submaximal stimulatory concentrations of IL-2 (2 or 20 U/ml) in the presence of IL-10, using an effector-to-target ratio of 5:1, with the results shown in Table 5 in which standard errors are shown beneath the mean values.

TABLE 5

Induction of Lymphokine-Activated Cytolytic
Activity (expressed as % lysis[a]) in Human Peripheral
Blood Mononuclear Cells by Co-Incubation with IL-10 and IL-2

| | | Incubation Conditions[b] | | | |
|---|---|---|---|---|---|
| Donor | medium | 2U IL-2 | 4 ng IL-10 | IL-10 + IL-2 | 20U IL-2 |
| 1 | 0.0 | 3.3 | 3.7 | 15.9 | 24.6 |
| 2 | 2.6 | 7.6 | 3.8 | 23.5 | 41.0 |
| 3 | 6.1 | 5.0 | 13.3 | 17.7 | 11.4 |
| 4 | 3.3 | 50.1 | 51.6 | 68.7 | 80.0 |
| 5 | 2.4 | 9.4 | 12.8 | 29.3 | 45.7 |
| 6 | 9.9 | 28.9 | 16.0 | 38.8 | 67.1 |
| Mean | 4.1 ± 1.42 | 17.4 ± 4.1 | 16.8 ± 7.2 | 32.3 ± 7.2 | 44.9[c] ± 10.4 |

[a]Percent lysis of [$^{51}$Cr] Daudi targets in standard chromium release assay at an effector:target cell ratio of 5:1. Data are represented as the mean of triplicate determinations.
[b]Human peripheral blood mononuclear cells prepared from normal donors were treated with 4 ng/ml IL-10 and 2 U/ml IL-2 for 3 days before determination of cytolytic activity.
[c]No significant difference between cytolytic activity in donor PBMCs treated with IL-10 and IL-2 compared to 20 U/ml IL-2 alone at $p \leq 0.05$ as determined by Student's t-test.

As shown in Table 5, there was an additive increase in LAK activity (effector cell:target cell ratio of 5:1) following co-incubation with 2 U/ml IL-2 and 4 ng/ml IL-10. This level of activity, which was significantly greater than that seen with either cytokine alone, approached the level produced using a 10-fold higher concentration of IL-2. This result was statistically significant at $p \leq 0.05$ as determined by the Student's t-test.

b. Simultaneous Incubation with IL-10 and α-IFN

PBMCs co-incubated with IL-10 and α-IFN display a similar additive increase in lytic activity against Daudi, but not NK target cells. This is shown in Table 6, in which standard errors are shown beneath the mean values.

TABLE 6

Induction of Lymphokine-Activated Killer Cell Activity
(expressed as % lysis[a]) in Human Peripheral Blood
Mononuclear Cells by Co-incubation with IL-10 and α-IFN

| | | Incubation Conditions[b] | | |
|---|---|---|---|---|
| Donor | medium | αIFN | IL-10 | IL-10 + α-IFN |
| 1 | 4.4 | 7.9 | 17.8 | 35.7 |
| 2 | 1.0 | 11.7 | 15.4 | 32.0 |
| 3 | 1.6 | 12.3 | 5.5 | 26.4 |
| Mean | 2.3 ± 1.0 | 10.6 ± 1.4 | 12.6 ± 3.8 | 31.4 ± 2.7 |

[a]Percent lysis of [$^{51}$Cr] Daudi targets in standard chromium release assay at an effector:target cell ratio of 10:1. Data are represented as the mean of triplicate determinations.
[b]Human peripheral blood mononuclear cells prepared from normal donors were treated with 4 ng/ml IL-10 and 100 U/ml α-IFN for 3 days before determination of cytolytic activity.

The differences observed in cytolytic activity induced in donor PBMCs by IL-10 and α-IFN compared to that induced by IL-10 or α-IFN alone were statistically significant at p<0.05 as determined by the Student's t-test.

In contrast, concomitant incubations with IL-10 and IL-4, IL-5, GMCSF or γ-IFN were no more effective than IL-10 alone (data not shown).

Sequential Incubations with IL-10 and IL-2

Using the procedures described above, PBMCs were maintained in medium alone or medium supplemented with IL-10. After two days, IL-2 was added to a final concentration of 2 or 20 U/ml. Cytotoxic activity against Daudi cells was assessed following an additional overnight incubation.

The results from a 5-donor pool are shown in Table 7, in which standard errors of the mean are shown beneath the mean values.

TABLE 7

Induction of Lymphokine-Activated Cytolytic Activity
(expressed as % lysis[a]) in Human Peripheral Blood
Mononuclear Cells by Pre-incubation with IL-10 Followed by IL-2

| Donor | Pre-Incubation Conditions[b] | | | |
|---|---|---|---|---|
| | medium | IL-10[c] | IL-2[d] | IL-10 + IL-2[e] |
| 1 | 29.7 | 21.1 | 44.8 | 116 |
| 2 | 5.5 | 18.3 | 12.2 | 20.7 |
| 3 | 14.7 | 58.1 | 74.5 | 100 |
| 4 | 26.2 | 59.5 | 54.3 | 81.9 |
| 5 | 4.8 | 28.2 | 22.5 | 40.6 |
| Mean | 16.2 ± 5.1 | 37.0 ± 9.0 | 41.7 ± 11.4 | 71.8 ± 17.9 |

[a]Percent lysis of [$^{51}$Cr] Daudi target cells in standard chromium release assay at an effector:target cell ratio of 5:1. Data are represented as the mean of triplicate determinations.
[b]Human peripheral blood mononuclear cells prepared from normal donors were maintained in medium supplemented with 4 ng/ml IL-10 for 2 days before addition of 2 U/ml IL-2. Cytolytic activity was determined following additional overnight incubation.
[c]Donor PBMCs were incubated with IL-10 for 3 days.
[d]Donor PBMCs were incubated in medium alone before adding IL-2.
[e]Donor PBMCs were incubated with IL-10 for 2 days before adding 20 U of IL-2

As shown in Table 7, in the groups where donor PBMCs were pre-treated with IL-10 before addition of IL-2, an approximately 2-fold higher level of cytolytic activity was observed (71.8+/−17.9%), compared to the level observed in cultures maintained in complete medium only before adding IL-2 (41.7% +/−11.4). The differences observed between samples pre-treated with IL-10 and those not treated with IL-10 were statistically significant at $p \leq 0.14$.

A similar pattern of enhanced cytolytic activity was seen in sequential incubations with IL-10 followed by α-IFN (data not shown).

IL-10 and IL-4 Blockage of IL-2-Induced Cytotoxicity

PBMCs from six human donors were cultured in medium containing 20 U/ml IL-2 alone, 20 U/ml IL-2 plus 1000 U/ml IL-4, or 20 U/ml IL-2 plus 1000 U/ml IL-4 plus 4 ng/ml IL-10. The results are shown in Table 8, in which standard errors of the mean are shown under the mean values.

TABLE 8

Antagonism by IL-10 of the Blockade by IL-4 of
IL-2-induced Lymphokine-Activated Cytolytic Activity
(expressed as % lysis[a]) in Human Peripheral Blood Mononuclear Cells

| Donor | Medium | IL-2[b] | IL-2[c] + IL-4 | IL-2[d] + IL-4 + IL-10 |
|---|---|---|---|---|
| 1 | 12.7 | 27.6 | 35.0 | 45.7 |
| 2 | 5.4 | 26.3 | 17.5 | 33.7 |
| 3 | 1.7 | 25.1 | 14.1 | 36.0 |
| 4 | 3.8 | 29.6 | 14.1 | 22.1 |
| 5 | 3.3 | 47.1 | 17.1 | 63.8 |
| 6 | 6.6 | 49.5 | 20.6 | 40.8 |
| Mean | 5.5 ± 1.6 | 34.2 ± 4.5 | 19.7 ± 3.2 | 40.3 ± 5.7 |

[a]Percent lysis of [$^{51}$Cr] Daudi targets in standard chromium release assay at an effector:target cell ratio of 20:1. Data are represented as the mean of triplicate determinations.
[b]Human peripyeral blood mononuclear cells isolated from normal donors were treated with 20 U/ml IL-2 for 3 days.
[c]Donor PBMCs were incubated with 20 U/ml IL-2 and 100 U/ml human IL-4 for 3 days.
[d]Donor PBMCs were incubated with 20 U/ml IL-2, 1000 U ml human IL-4, and 4 ng/ml IL-10

The data of Table 8 show that following treatment with 20 U/ml IL-2 alone, about 34.2% lysis of LAK-sensitive targets was observed. When 1000 U/ml human IL-4 was included at the start of the incubation period, cytolytic capacity was suppressed approximately 2-fold. This suppression by IL-4 was not observed, however, if 4 ng/ml IL-10 was added during the first 24 hours of incubation. There was no significant difference between the results produced by IL-2 alone and by all three cytokines together ($p \leq 0.05$, as determined by Student's t-test), indicating that antagonism by IL-10 of the blockage was essentially complete.

Many modifications and variations of this invention can be made without departing from its spirit and scope, as will become apparent to those skilled in the art. The specific embodiments described herein are offered by way of example only, and the invention is to be limited only by the terms of the appended claims.

What is claimed is:

1. A method for treating cancer comprising administering activated peripheral blood mononuclear cells (PBMCs) to a patient afflicted with cancer in an amount effective to cause regression of such cancer, said PBMCs having been activated with Interleukin-10 (IL-10) in the absence of Interleukin-2 (IL-2).

2. The method of claim 1 which further comprises concomitant or subsequent administration of an effective amount of IL-10.

3. The method of claim 2 in which the IL-10 used for PBMCs activation and concomitant or subsequent administration is human IL-10.

4. The method of claim 3 in which the IL-10 is administered in combination with an amount of IL-2 sufficient to augment LAK cell activation but not to cause toxic side effects attributable to the use of IL-2 alone.

5. The method of claim 4 in which the IL-10 is administered prior to the administration of IL-2.

6. The method of claim 3 in which the IL-10 is administered in combination with an amount of α-IFN sufficient to augment LAK cell activation.

7. The method of claim 3 in which the IL-10 is administered in combination with (a) an amount of IL-2 sufficient to augment LAK cell activation but not to cause toxic side effects attributable to the use of IL-2 alone and with (b) an amount of α-IFN sufficient to augment LAK cell activation.

8. The method of claim 3 in which the amount of IL-10 administered is in the range of about 10 U/kg body weight per day to about $10^8$ U/kg of body weight per day.

9. The method of claim 8 in which the IL-10 is administered intravenously.

10. The method of claim 3 in which the number of activated PBMCs administered is in the range of about $10^6$ to about $10^{12}$ cells.

11. The method of claim 10 in which the cells are administered by intravenous infusion.

12. The method of claim 3 which is performed in conjunction with the use of one or more chemotherapeutic agents or radiation therapy.

13. A pharmaceutical composition comprising peripheral blood mononuclear cells (PBMCs) activated extracorporeally with IL-10 in the absence of IL-2.

14. The pharmaceutical composition of claim 13 further comprising IL-10.

15. The pharmaceutical composition of claim 14, further comprising IL-2.

16. The pharmaceutical composition of claim 14, further comprising α-IFN.

17. The pharmaceutical composition of claim 14, further comprising IL-2 and α-IFN.

18. A method of rendering isolated peripheral blood mononuclear cells (PBMCs) cytolytic comprising contacting isolated PBMCs with IL-10 in the absence of IL-2.

19. The method of claim 18, wherein the PBMCs are contacted with IL-10 and α-IFN.

* * * * *